(12) United States Patent
Py (10) Patent No.: US 8,746,278 B2
(45) Date of Patent: Jun. 10, 2014

(54) CONNECTOR AND RELATED METHOD

(76) Inventor: Daniel Py, Larchmont, NY (US)

( * ) Notice: Subject to any disclaimer, the term of this patent is extended or adjusted under 35 U.S.C. 154(b) by 206 days.

(21) Appl. No.: 13/213,969

(22) Filed: Aug. 19, 2011

(65) Prior Publication Data

US 2012/0042971 A1   Feb. 23, 2012

Related U.S. Application Data

(60) Provisional application No. 61/375,393, filed on Aug. 20, 2010, provisional application No. 61/377,285, filed on Aug. 26, 2010.

(51) Int. Cl.
*E03B 1/00* (2006.01)
*F16K 31/44* (2006.01)

(52) U.S. Cl.
USPC .................. 137/614; 251/340; 251/352

(58) Field of Classification Search
USPC ............ 137/614.05, 614.06, 614, 614.01, 137/614.02; 251/340, 341, 349, 352, 149.8, 251/149.9
See application file for complete search history.

(56) References Cited

U.S. PATENT DOCUMENTS

| | | | | |
|---|---|---|---|---|
| 263,330 | A * | 8/1882 | Franklin | 251/340 |
| 2,556,583 | A * | 6/1951 | Hinz | 251/352 |
| 2,709,566 | A * | 5/1955 | Davis | 251/148 |
| 4,271,865 | A | 6/1981 | Galloway et al. | |
| 4,366,816 | A | 1/1983 | Bayard et al. | |
| 4,509,554 | A * | 4/1985 | Failla | 137/614.05 |
| 4,554,948 | A * | 11/1985 | Bergmann | 137/625.31 |
| 4,750,674 | A | 6/1988 | Chow et al. | |
| 4,848,403 | A * | 7/1989 | Pilolla et al. | 137/625.31 |
| 4,949,745 | A * | 8/1990 | McKeon | 137/15.09 |
| 5,419,354 | A * | 5/1995 | Krynicki | 137/1 |
| 5,884,648 | A * | 3/1999 | Savage | 137/1 |
| 5,895,029 | A * | 4/1999 | Lacout | 251/353 |
| 6,349,858 | B1 | 2/2002 | Kingsford et al. | |
| 6,585,229 | B2 * | 7/2003 | Cote et al. | 251/149.1 |
| 2007/0204924 | A1* | 9/2007 | Delgiacco et al. | 137/625.31 |
| 2009/0108224 | A1* | 4/2009 | Clasen et al. | 251/315.04 |
| 2009/0232586 | A1* | 9/2009 | Diodati et al. | 403/14 |

OTHER PUBLICATIONS

International Search Report and Written Opinion of the International Searching Authority for International Application No. PCT/US2011/48483, mailed Jan. 5, 2012.

* cited by examiner

*Primary Examiner* — John Rivell
*Assistant Examiner* — David Colon Morales
(74) *Attorney, Agent, or Firm* — McCarter & English LLP (57) ABSTRACT

A connector for transferring a fluid includes a first connector and a second connector. Each connector includes a first outer portion including a first obstructive portion and defining a first fluid passageway for receiving a fluid therein. Each connector further includes a first central nozzle coupled to the first outer portion. The central nozzle includes a first engagement member. The first central nozzle is movable between a first position and a second position with rotation of the first outer portion. In the first position, the first obstructive portion and the first engagement portion substantially overlap to impede fluid flow through the first fluid passageway. In the second position, at least one of the first engagement member and the first obstructive member is displaced to allow fluid flow through the first fluid passageway.

19 Claims, 11 Drawing Sheets

SECTION A-A
FIG. 4A

STEP 2: ROTATE SECTION A-A

CONNECTOR AND RELATED METHOD

CROSS-REFERENCE TO RELATED APPLICATIONS

This patent application claims the benefit under 35 U.S.C. §119(e) of U.S. Provisional Application Ser. No. 61/375,393, filed Aug. 20, 2010, and U.S. Provisional Application Ser. No. 61/377,285, filed Aug. 26, 2010, both of which are entitled "Clean Connector And Related Method", and are hereby expressly incorporated by reference as part of the present disclosure.

FIELD OF THE INVENTION

The present invention relates to fluid connectors and methods of transferring fluids or other material, and more particularly, relates to fluid connectors and methods for transfer of fluids in a manner that maintains the transferred fluid clean, aseptic, sterile, or in another desired condition.

BACKGROUND INFORMATION

A typical fluid connector includes a male connector that is received within a female connector to place the two connectors in fluid communication with each other. The male and female connectors may be threadedly engaged, snap fit, or otherwise releasably connected to each other to allow for interconnection and disconnection. Each connector is coupled in fluid communication with a respective fluid passageway, such as a tube or fluid chamber, in order to place the fluid passageways in fluid communication with each other and allow the passage of fluids therebetween. Typical fluid connectors include outer surfaces which may become contaminated when exposed to the ambient atmosphere. Moreover, airborne germs may contaminate the inner portions of typical fluid connectors, which include passageways that remain open before and after use, or during storage.

One approach to preventing such contamination is to wipe the fluid-contacting surfaces of the male and female connectors with an alcohol wipe or other disinfectant prior to interconnection. One drawback of this approach is that it may not remove all germs on the fluid-contacting surfaces, or the inner surfaces in cases where airborne germs have traveled inside the connector. Another drawback of this approach is that the fluid-contacting surfaces may become contaminated after the wipe is applied but prior to interconnection of the male and female connectors. Yet another drawback of this approach is that it can be time consuming and considered a nuisance, and therefore unreliable in practice.

Such contamination can give rise to significant problems. If used in a hospital or other medical facility, such as to transfer sterile drugs or other fluids intended for intravenous injection, for example, any such contamination can lead to viral and other types of infections, serious illnesses, and death. In food processing applications, this can lead to contamination of previously-sterile food products, and if such contaminated products are ingested, they can cause infections and/or illnesses. In industrial applications, it may be necessary to prevent a toxic fluid passing through a connector from contaminating the ambient atmosphere, an operator handling the connector, and/or other surfaces that might be located external to the connector. If the fluid-contacting surfaces of the connector are exposed to human contact, or surfaces that come into human contact, for example, this can lead to possible injury and/or illnesses.

Accordingly, it is an object of the present invention to overcome one or more of the above-described drawbacks and/or disadvantages of the prior art.

SUMMARY OF THE INVENTION

In accordance with a first aspect, the present invention is directed to a fluid connector formed of a first or female connector and a second or male connector. Each of the connectors include a first outer portion including a first obstructive portion and defining a first fluid passageway for receiving a fluid therein. Each of the connectors further include a first central nozzle coupled to the first outer portion. The central nozzle includes a first engagement member. The first central nozzle is movable between a first position and a second position with rotation of the first outer portion. In the first position, the first obstructive portion and the first engagement portion substantially overlap to impede fluid flow through the first fluid passageway. Rotation of the outer portion may move the connector to a second position where the first engagement member and/or the first obstructive member is displaced to allow fluid flow through the first fluid passageway.

In another aspect, the first and second connectors are engageable and movable between non-connected and connected positions. In the non-connected positions, the first fluid passageway and second fluid passageway are obstructed, and in the connected position, the first fluid passageway and second fluid passageway are in fluid communication with one another.

In accordance with another aspect, the present invention is directed to a method comprising the following steps:

(i) positioning or maintaining a first connector connected to one end of a first conduit in a closed position to, in turn, maintain a fluid hermetically sealed within the first conduit, wherein a first nozzle of the first connector is in fluid communication with the first conduit and is recessed within a first housing of the first connector to prevent contamination of the first nozzle;

(ii) interconnecting the first connector to a second connector connected to one end of a second conduit and positioned in a closed position that maintains the second conduit sealed with respect to ambient atmosphere, wherein a second nozzle of the second connector is in fluid communication with the second conduit and is recessed within a second housing of the second connector to prevent contamination of the second nozzle; and (iii) moving, such as by rotating, at least one of the first and second connectors or portions thereof from the closed to an open position and, in turn, placing the first and second nozzles in fluid communication with each other to allow fluid to flow from the first conduit, through the first and second nozzles, and into the second conduit without exposing the fluid to ambient atmosphere.

In accordance with a further aspect of the present invention, the method includes introducing the fluid into the first conduit and, in turn, allowing the fluid to flow from the first conduit, through the first and second nozzles, and into the second conduit without exposing the fluid to ambient atmosphere. In some embodiments of the present invention, the interconnecting step includes engaging first and second engagement portions of the first and second nozzles, such as by frictional engagement, and preventing rotation of the first and second engagement portions relative to each other, and the moving step includes rotating at least one of the first and second nozzles relative to the other to move from the closed to the open position.

One advantage of the present invention is that when not connected, the connector remains in the closed position to prevent fluid flow or ingress of airborne germs or bacteria. Then, when connected, the connectors are opened to allow fluid flow. Accordingly, the present invention is particularly advantageous for fluid transfer in a manner that maintains the transferred fluid clean, aseptic, sterile, or in another desired condition. For example, two fluid conduits can be interconnected with the connector of the present invention to reduce the likelihood of contamination from germs on the outer surfaces of the connectors.

Other objects and advantages of the present invention, and/or of the currently preferred embodiments thereof, will become more readily apparent in view of the following detailed description of the currently preferred embodiments and accompanying drawings.

DETAILED DESCRIPTION OF EMBODIMENTS OF THE INVENTION

Figure 1A:
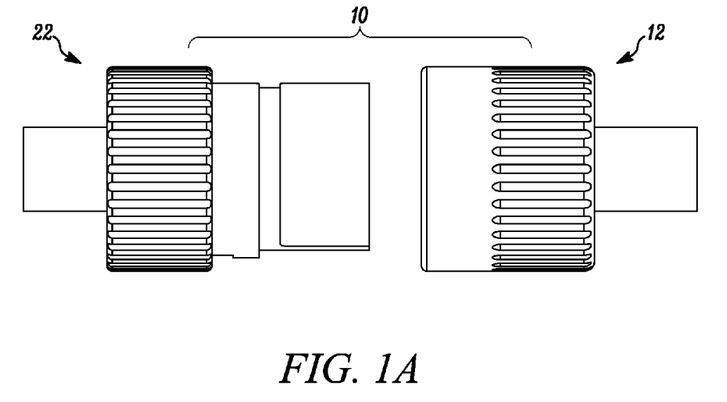
FIG. 1A is a schematic side view of a connector embodying the present invention showing the male and female connectors in a non-connected state with the connectors in their closed positions.
Figure 1B:
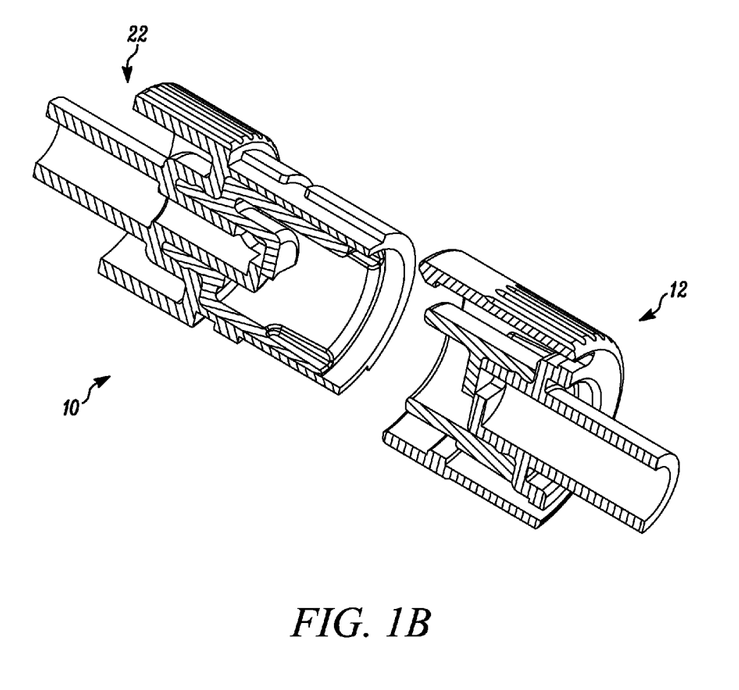
FIG. 1B is a perspective, cross-sectional view of the connector of FIG. 1A showing the male and female connectors in a non-connected state with the connectors in their closed positions.
Figure 1C:
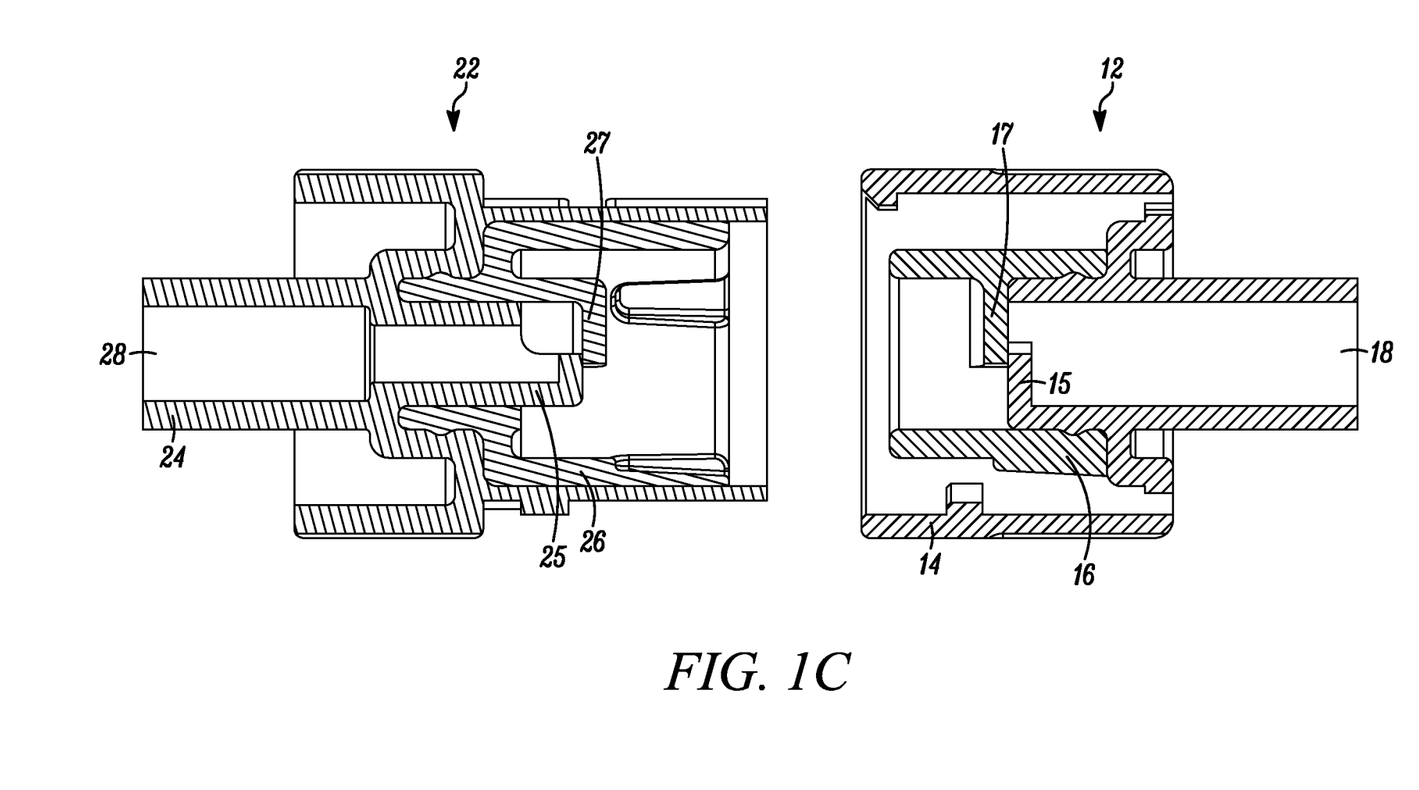
FIG. 1C is a cross-sectional view of the connector of FIG. 1A showing the male and female connectors in a non-connected state with the connectors in their closed positions.

In FIG. 1A-C, a connector embodying the present invention is indicated generally by the reference numeral 10. The connector 10 comprises a first or female connector 12 and a second or male connector 22. As shown in FIG. 1C, the first connector 12 includes a first fluid passageway 18 for receiving a fluid therein. The second connector 22 includes a second fluid passageway 28 for receiving a fluid therein. The first or female connector 12 includes a first outer portion 14 and the second or male connector 22 includes a second outer portion 24. The first and second outer portions 14, 24 may be formed of any of numerous different materials that are currently known or that later become known for this purpose, such as a suitable plastic, including, for example, a thermoplastic.

In some embodiments, the outer portion 14 of the first connector 12 and the outer portion 24 of the second connector 22 are complementary. In at least some embodiments, the first connector 12 is configured to receive the second connector 22 therein. It will be understood by those of ordinary skill in the art that, as used in the present description, the terms "male" and "female" with respect to connectors are not limiting and that any type of mating or engagement of the two connectors may be achieved as contemplated by the present invention. For example, as may be recognized by those of ordinary skill in the pertinent art based on the teachings herein, the first and second connectors 12, 22 can be releasably connected to each other in any of numerous different ways that are currently known, or that later become known, such as by a threaded connection, snap fit, or other releasable interconnection.

FIG. 1B is a perspective, cross-sectional view of the connector 10 of FIG. 1A showing the male and female connectors in a non-connected state. FIG. 1C is a cross-sectional view of the connector 10 of FIG. 1A showing the male and female connectors in a non-connected state. As shown in FIG. 1C, the first connector 12 includes a first central nozzle 16 located or otherwise formed within the first outer portion 14. In some embodiments, the first central nozzle 16 is formed of the same material as the first outer portion 14. In at least some embodiments, the first central nozzle 16 is formed of a different material than the first outer portion 14.

It will be understood that the outer portion 14 and the central nozzle 16 may be manufactured using a variety of techniques. In some embodiments, the outer portion 14 is initially formed and the central nozzle 16 is insert-molded onto the outer portion 14. Other injection molding techniques also may be used to manufacture portions of the first and second connectors such as, for example, co-molding and overmolding. The outer portion 14 and the central nozzle 16 may be formed such that one of the pieces is able to move or rotate relative to the other. The ability of outer portion 14 and the central nozzle 16 to move relative to the other is significant for creating a fluid flow path as will be described below with reference to FIGS. 3A and 3B.

As shown in FIG. 1C, the second connector 22 includes an outer portion 24 and a second central nozzle 26 similar to that of the first connector 12. Like the first connector 12, the second connector 22 may be formed through insert-molding techniques. It will be understood that the parts, processes and description of the first connector 12 may be applied to the second connector 22, and vice versa.

As shown in FIG. 1C, the first connector 12 and the second connector 22 define a first fluid passageway 18 and a second fluid passageway 28, respectively. In the illustrated embodiments, the first and second fluid passageways 18, 28 are defined as longitudinal lumens, axially extending through the connectors 12, 22. It will be understood that various configurations of the first and second fluid passageways 18, 28 may be chosen as desired. In FIGS. 1B and 1C, the first and second connectors are non-connected and are in the closed position. Each of the outer portions 14 and 24 includes obstructive portions 15 and 25, respectively. The obstructive portions 15, 25 may take any of numerous different configurations that are currently known or that later become known for performing their functions as described herein, such as any of numerous different types of ridges, flanges or projections that block a portion of the respective fluid passageway. As can be appreciated from FIGS. 1B and 1C, the obstructive portions 15 and 25 preferably define a portion of the outer portions 14, 24 that normally projects across a portion of the fluid passageways 18 and 28, respectively, to close the respective fluid passageway. In the illustrated embodiment, in the closed position, each obstructive portions 15, 25 hermetically seals the interior of the respective connector and conduit from the ambient atmosphere and prevents fluid transfer between the two connectors.

The central nozzles 16 and 26 further include projections similar to the obstructive portions 15 and 25. In the illustrated embodiment, the first central nozzle 16 includes a first engagement portion 17 and the second central nozzle 26 includes a second engagement portion 27. The engagement portions 17, 27 are normally projecting portions, which impede or block a portion of the first and second passageways 18, 28, respectively, when in the closed position. In some embodiments, the first and second connectors 12, 24 are formed such that in the closed position, the obstructive portions 15, 25 of the outer portions 14, 24 and the engagement portions 17, 27 of the central nozzles 16, 26 completely block fluid flow through the fluid flow passageways 18, 28. If desired, the first and second connector may be configured to only partially block fluid flow in the closed position. In at least some embodiments, the engagement portions 17, 27 and the obstructive portion 15, 25 radially overlap in the closed position, as shown, to ensure a hermetic seal and otherwise impede fluid flow.

Figure 2A:
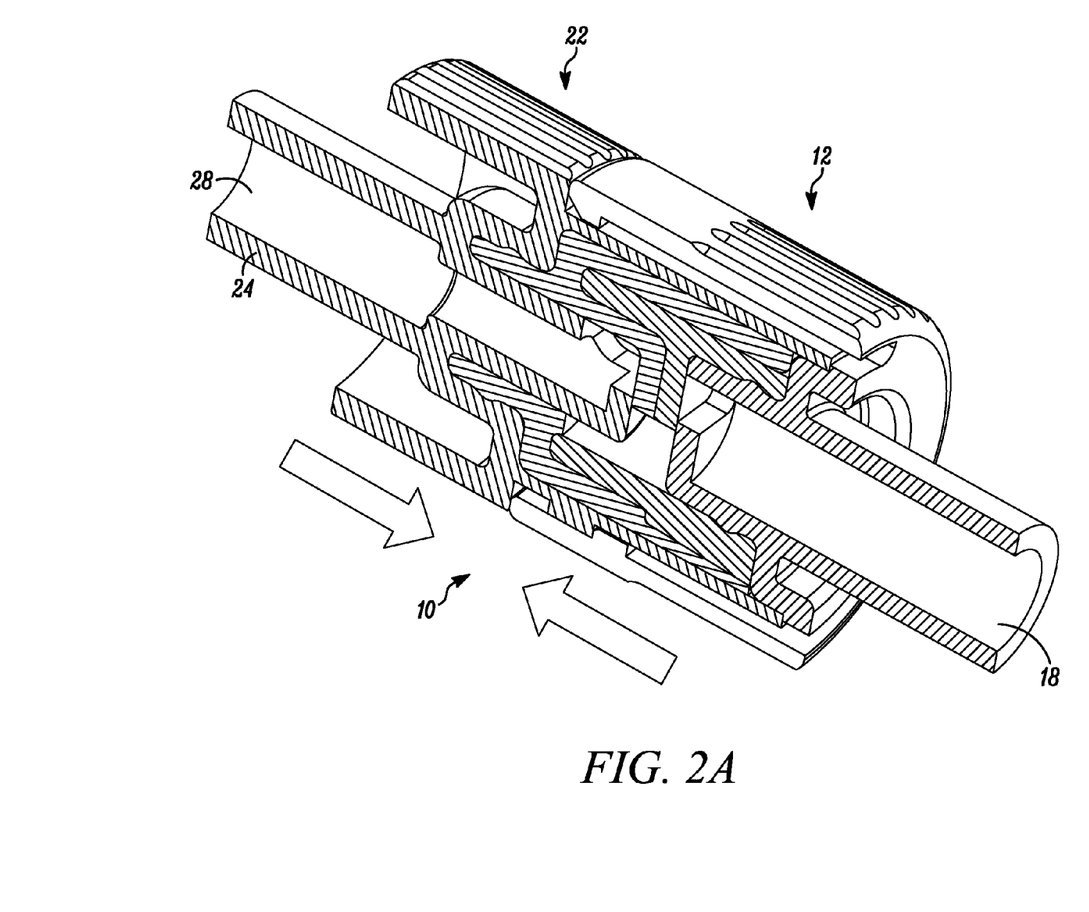
FIG. 2A is a perspective, cross-sectional view of the connector of FIGS. 1A-C showing the mating of the male and female connectors, as indicated by the arrows, wherein the male connector housing is initially received within the female connector housing and the connectors are still in the closed positions.
Figure 2B:
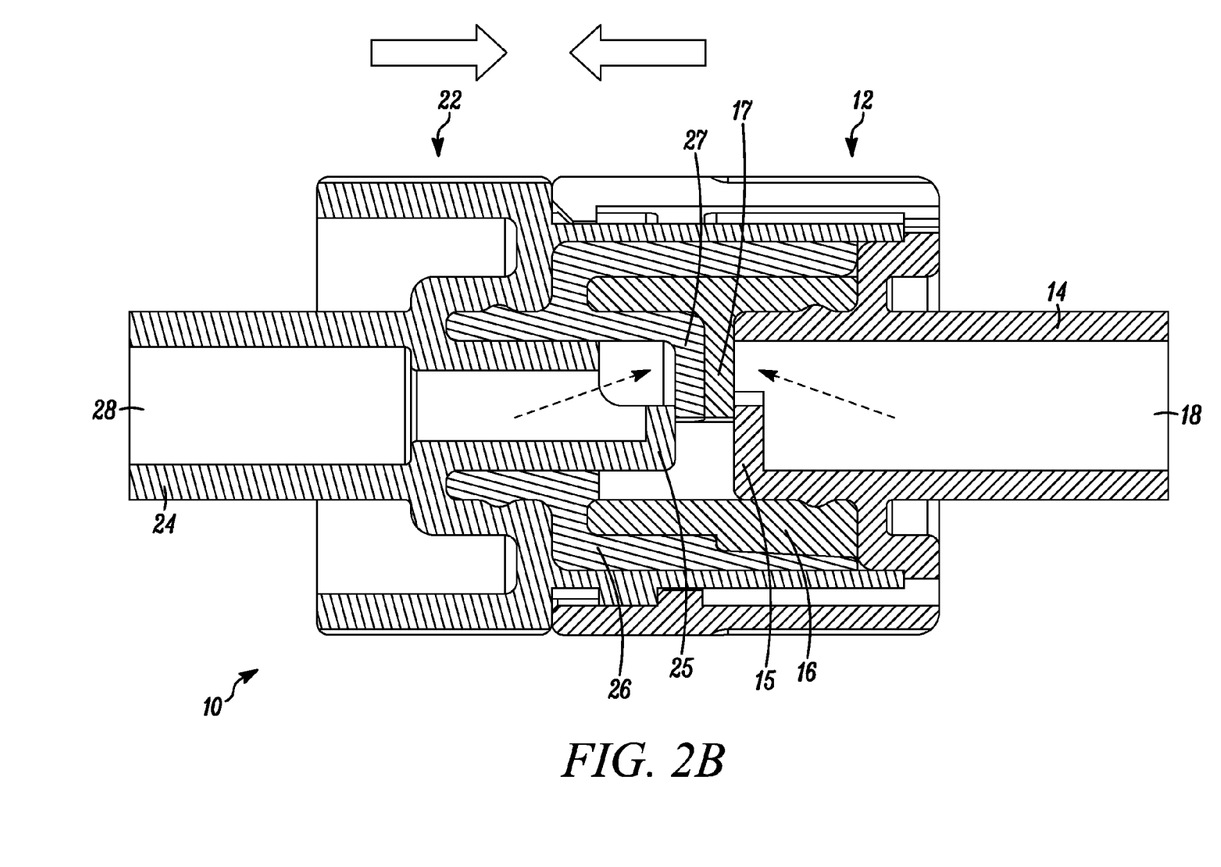
FIG. 2B is a cross-sectional view of the connector of FIGS. 1A-C further showing the mating of the male and female connectors, as indicated by the solid line arrows, wherein the male connector housing is initially received within the female connector housing and the connectors are still in the closed positions, as indicated by the two broken-line arrows.

FIGS. 2A and 2B are cross-sectional views of the connector of FIGS. 1A-C showing the mating of the male and female connectors, wherein the male connector housing is initially received within the female connector housing. As seen in FIGS. 2A and 2B, and as indicated by the arrows, the second connector 22 is received within the first connector 12 by bringing together the two connectors. As can be appreciated from FIGS. 2A and 2B, the first and second connector 12 and 22 are pushed together until the engagement portions 17, 27 of the central nozzles 16, 26 abut each other (FIG. 2B).

In the intermediate position shown in FIGS. 2A and 2B, the first and second connectors 12 and 22 are substantially radially aligned such that the first fluid passageway 18 and the second fluid passageway 28 are substantially aligned. The obstructive portions 15, 25 of the outer portions 14, 24 and the engagement portions 17, 27 of the central nozzles 16, 26 block the fluid passageways 18, 28 such that the two fluid passageways are not in fluid communication. As can be seen in the illustrated embodiments, the central nozzle 16 of the first female connector 12 and the central nozzle 26 of the second male connector 22 are engaged or mated when the two connectors are brought together. Thus, in this intermediate position, the two connectors remain in the closed position.

Figure 3A:
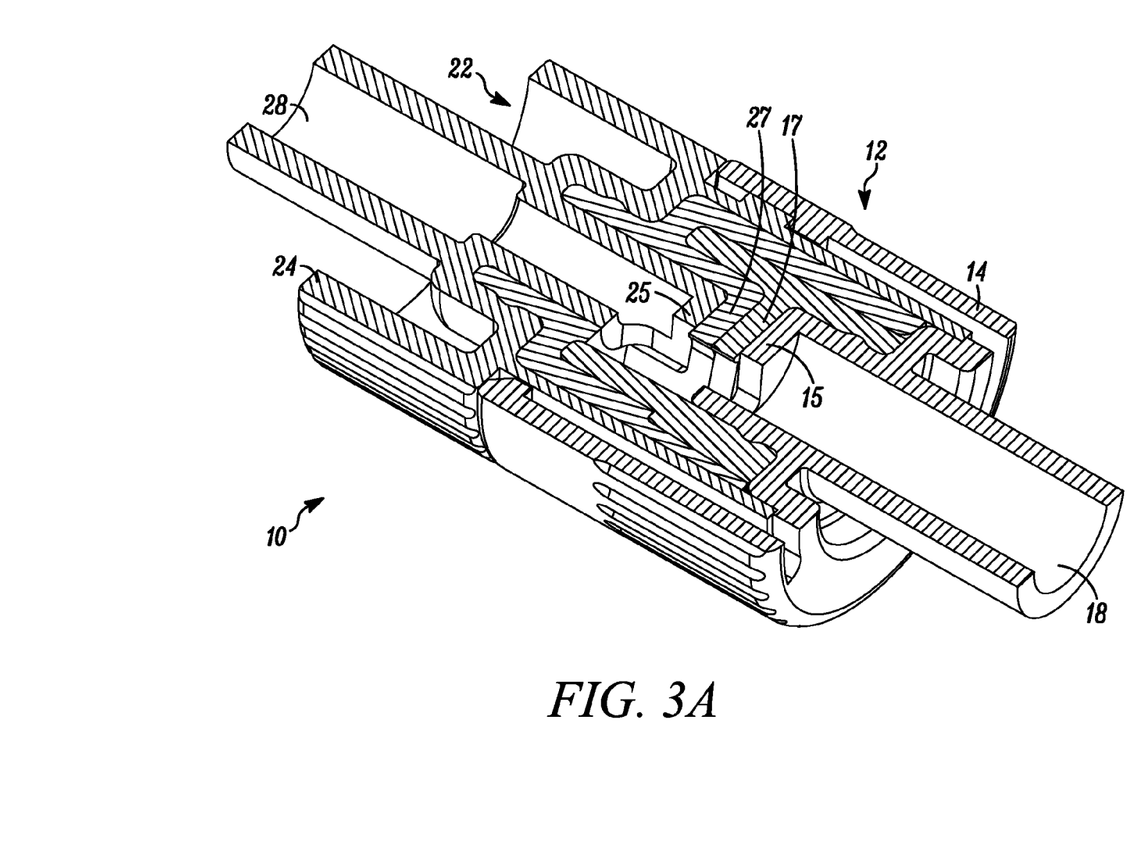
FIG. 3A is a perspective, cross-sectional view of the connector of FIGS. 1A-C after rotation of at least one of the connectors to move the connector to an open position having a fluid flow path through the connector.
Figure 3B:
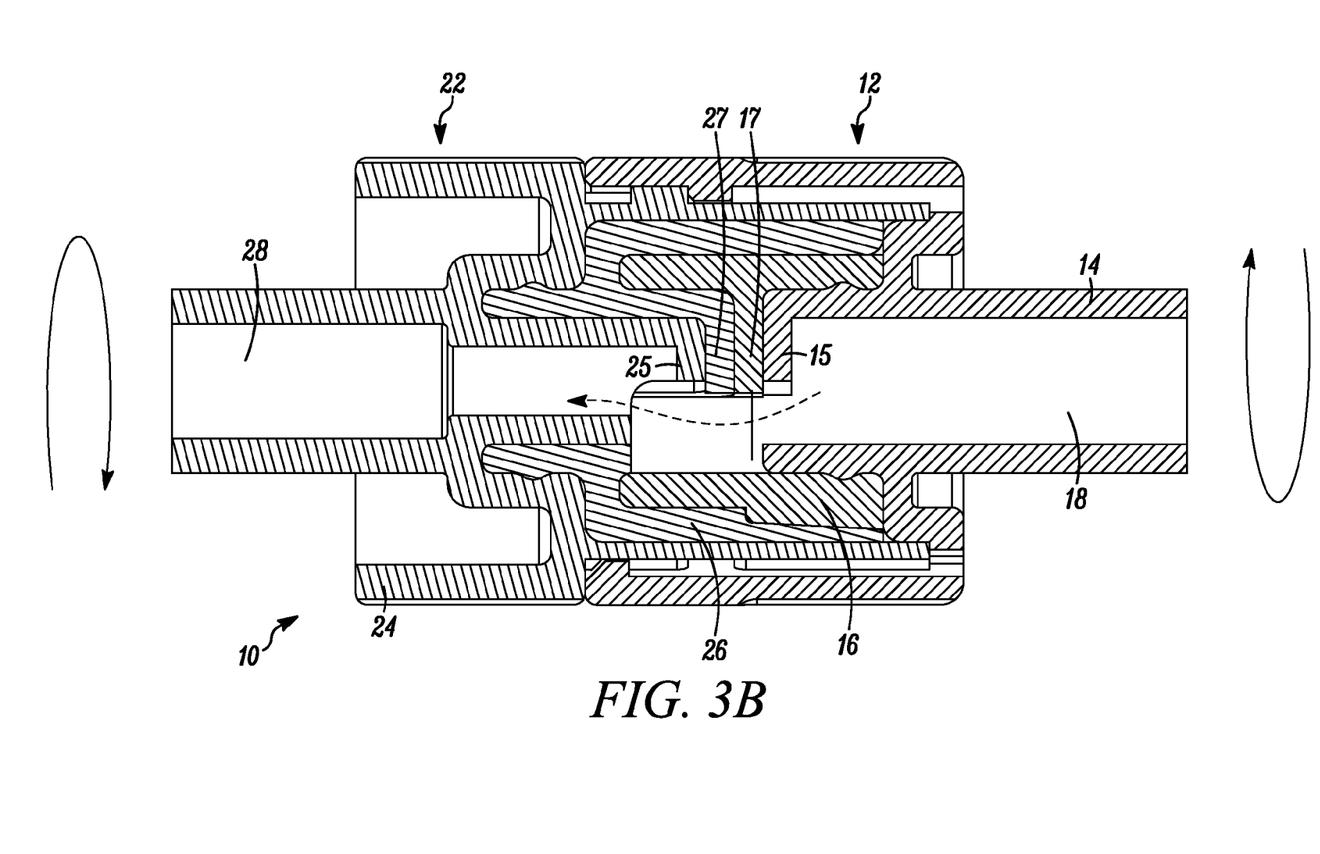
FIG. 3B is a cross-sectional view of the connector of FIGS. 1A-C after rotation of at least one of the connectors, as indicated by the solid line arrows, to move the connector to an open position having a fluid flow path through the connector, as indicated by the broken line arrow.
Figure 4A:
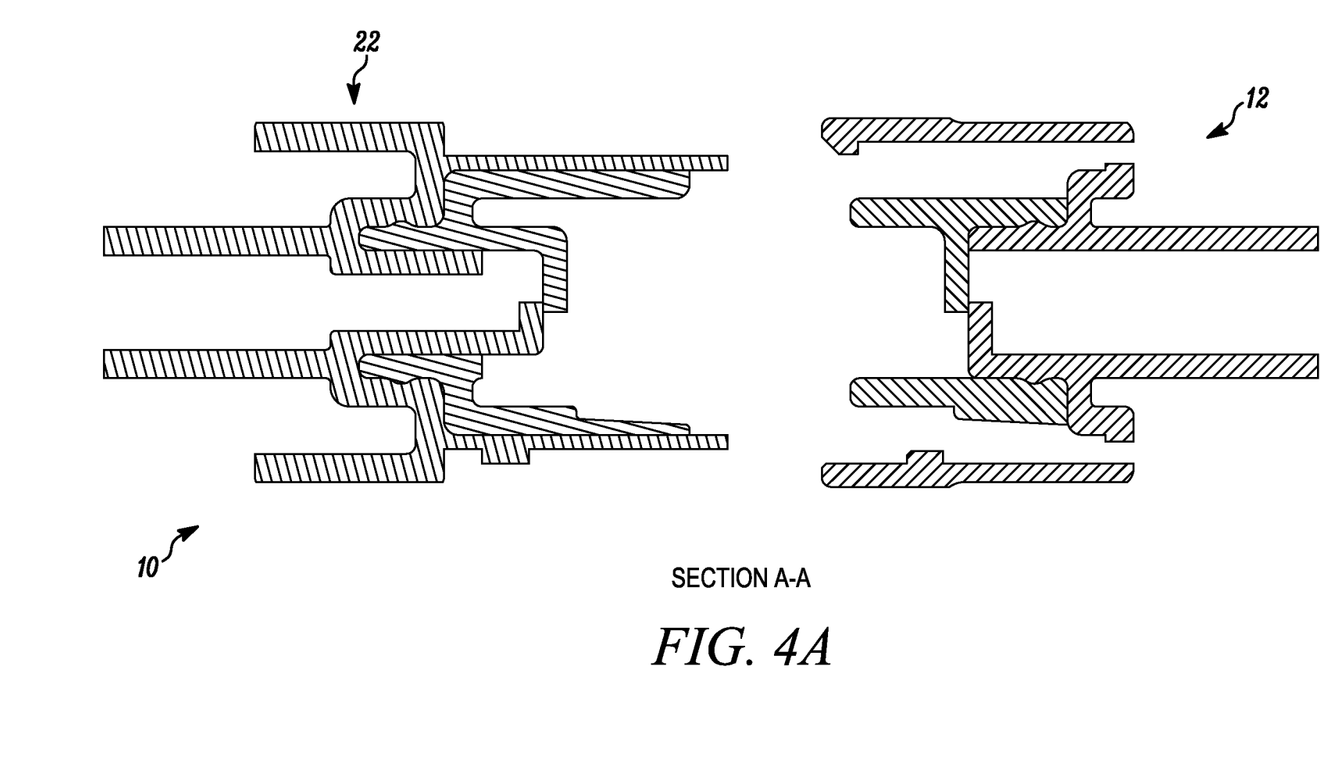
FIGS. 4A-4C are cross-sectional views of one embodiment of a connector embodying the present invention, with some parts not shown for clarity, illustrating the connector in a non-connected position, in a connected but closed position, and in a connected and open position, respectively, where in FIG. 4C the first and second fluid passageways of the first and second connectors are in fluid communication with one another.
Figure 4B:
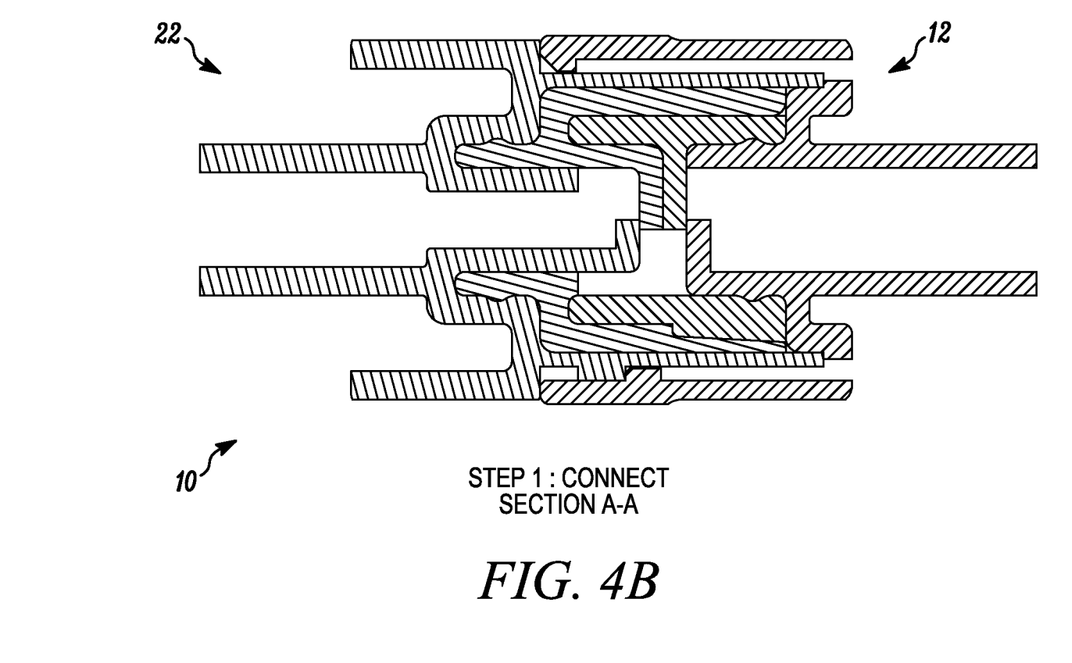
Figure 4C:
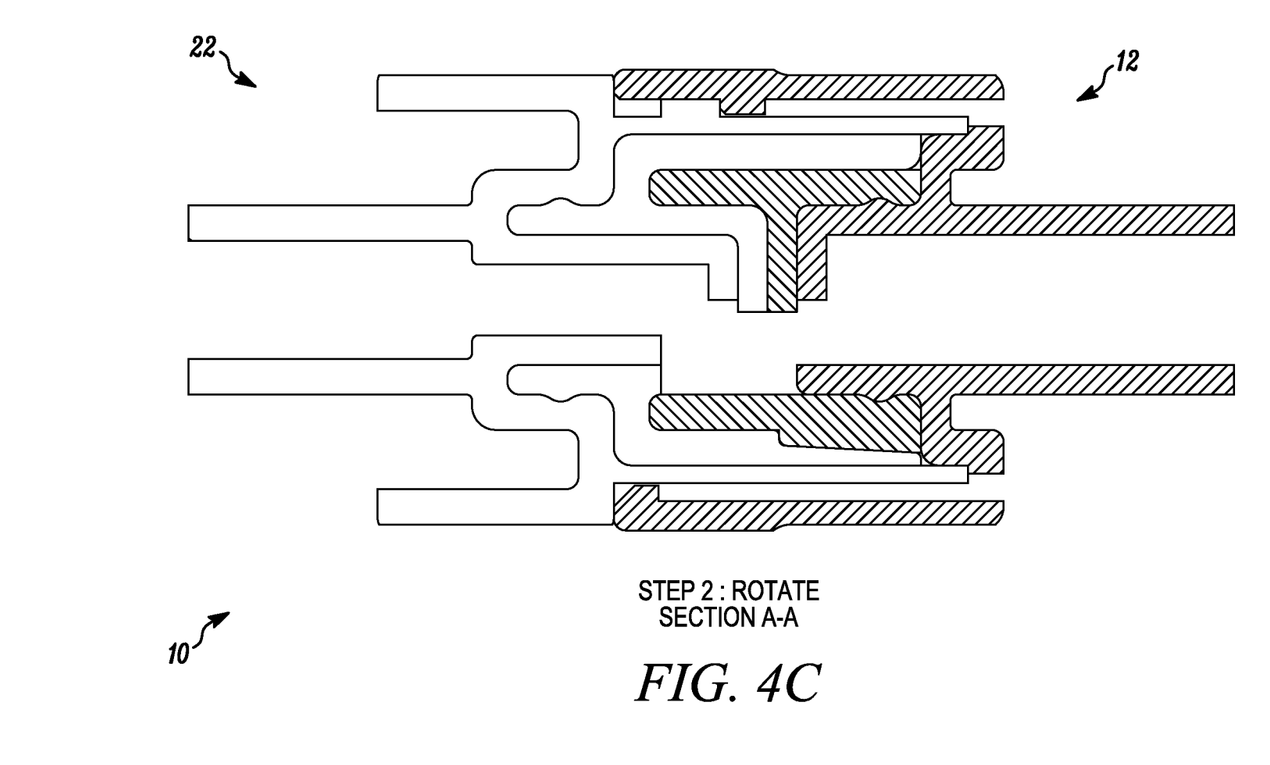

FIGS. 3A and 3B illustrate cross-sectional views of the connector of FIGS. 1A-C in the open position. After mating of the first and second connectors 12 and 22, and as indicated by the solid line arrows in FIG. 3B, one or both connector(s) may be twisted or rotated to move the connectors from a closed position to an open position and reveal a flow path as indicated by the broken line arrow in FIG. 3B. When the male connector 22 is fully engaged with the female connector 12, the engagement portions 17, 27 of the central nozzles 16, 26 are engaged in an abutting relationship with each other. In the illustrated embodiment, the engagement portions 17, 27 of the connectors are configured so that they do not rotate with respect to one another when so engaged. In some embodiments, the shape of the engagement portions 17, 27 is formed so that the two portions are locked together when engaged. In at least some other embodiments, a frictional engagement is formed between the two engagement portions 17, 27 to prevent the nozzle portions from rotating relative to one another when engaged. Thus, when the two engagement portions 17, 27 are paired, they may be pulled apart (i.e., in an axial direction) but not rotated with respect to one another. As can be understood by comparing the cross-sectional views of the intermediate position, e.g. FIGS. 2A and 2B, with the cross-sectional views of the fully open position, e.g. FIGS. 3A and 3B, the central nozzles 16, 26 remain in the same position before and after rotation of the two connectors because when the engagement portions 17, 27 are in abutting engagement their relative rotation is prevented, while relative rotation of the first and second outer portions 14, 24 is permitted.

As indicated by the solid line arrows in FIG. 3B, rotation of one or both connectors serves to open a fluid path between the two connectors 12, 22 as indicated by the broken line arrow. As seen in FIGS. 3A and 3B, when the connectors 12, 22 are rotated relative to each other, the outer portions 14, 24 of the connectors 12, 22 rotate while the central nozzles 16, 26 remain in the same position. Rotation of the outer portions 14, 24 also serves to angularly displace or rotate the obstructive portions 15, 25 of the outer portions 14, 24. Thus, looking at the first connector 12, it will be understood that after rotation, the central nozzle 16 remains in place while the outer portion 14 rotates to a second position. More specifically, the obstructive portion 15 of the outer portion 14 rotates from a first position to a second position adjacent to the engagement portion 17 of the first central nozzle 16. Likewise, the second obstructive portion 25 of the second outer portion 24 rotates to a second position adjacent to the second engagement portion 27 of the second central nozzle 26. In some embodiments, rotation of one or both of the connectors 12, 22 causes the obstructive portions 15, 25 and the engagement portions 17, 27 to align or become substantially aligned.

In the illustrated embodiments, when the obstructive portions 15, 25 are displaced from their first position to their second position, a fluid path is formed between the first passageway 18 and the second passageway 28, as indicated by the broken line arrow in FIG. 3B, so that fluid is able to flow or be transferred through the first and second connectors 12, 22 via the first and second passageways 18, 28. Thus, a significant advantage of the present invention is that the connectors 12 and 22 are maintained in a closed position in the non-connected position and actuated to an open position after interconnection and rotation.

The obstructive portions 15, 25 and the engagement portions 17, 27 thus provide a closed position when the connectors are not in use. While the connectors 12 and 22 are in the closed position, fluid or other material is incapable of flowing through the connectors as the fluid flow passageway is blocked. Another advantage of the present invention is that the obstructive portions 15, 25 and the engagement portions 17, 27 deter ingress of airborne germs or other contaminants into the passageways 18, 28. Instead, germs or other contaminants are blocked by the outer surfaces of the obstructive portions 15, 25 and the engagement portions 17, 27 in the closed position. This is because in the open position, the obstructive portions 15, 25 and the engagement portions 17, 27 are engaged with one another and not in contact with the fluid being transferred. For example, the outer surface of the first obstructive portion 15, which may have been exposed to a contaminant in the closed position, is moved to a position behind the first engagement member 17 in the open position. Thus, the fluid being transferred is not brought into contact with this outer surface of the first obstructive portion 15.

In some embodiments, the two-piece connector 10 is molded from a material that is non-bondable. The materials used for either or both the central nozzles 16, 26 and the outer portions 14, 24 may be rigid to allow rotation of one relative to the other. In at least some embodiments, the materials used include different shrinkage—e.g. that at least a portion of the connector 10 includes molded parts having materials that contract to different extents after cooling. In some embodiments, the outer portions 14, 24 have a shrinkage less than the shrinkage of the central nozzles 16, 26. This technique may be useful for providing the requisite level of friction between the components, such as between the engagement portions. In addition, in some embodiments, the central nozzles 16, 26 and outer portions 14, 24 are formed of a non-bondable material or formed of materials with different shrinkage. By using any one of these techniques, it is possible to provide a central nozzle 16, 26 that is able to rotate relative to the respective outer portion 14, 24. In some embodiments, dual sequential injection is used, e.g. the central nozzle 26 and outer portion 14 of the first connector 12 are formed simultaneously and the central nozzle 16 and outer portion 24 of the second connector 22 are formed simultaneously. In at least some embodiments, a non-rotary mold system is utilized for forming a portion of the connector 10.

Figure 5A:
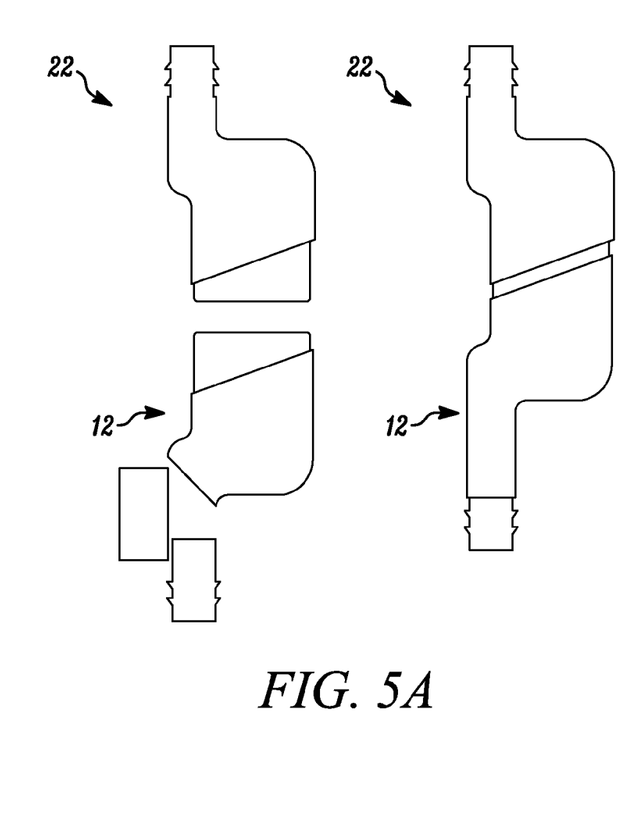
FIG. 5A is a schematic side view of a field-of-use differentiating clean connector for use with enteral applications having a predetermined diameter, interface and shape.
Figure 5B:
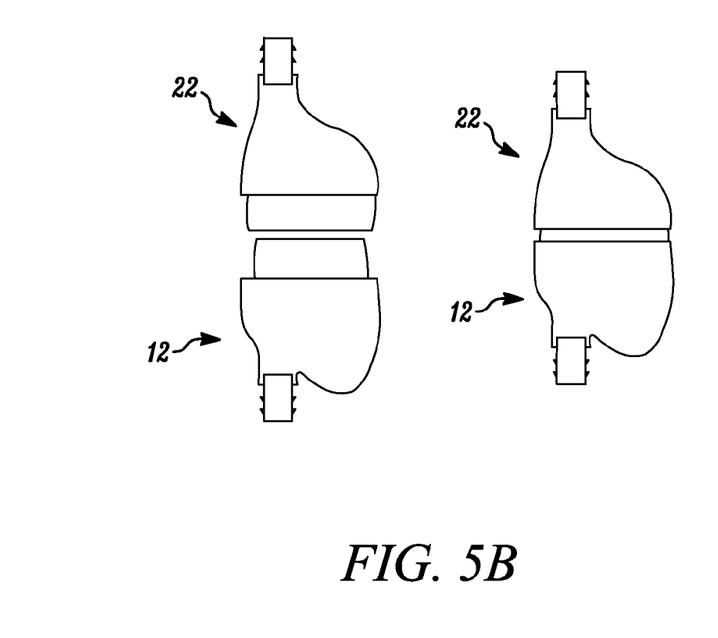
FIG. 5B is a schematic side view of a field-of-use differentiating clean connector for use with vascular applications having a predetermined diameter, interface and shape.
Figure 5C:
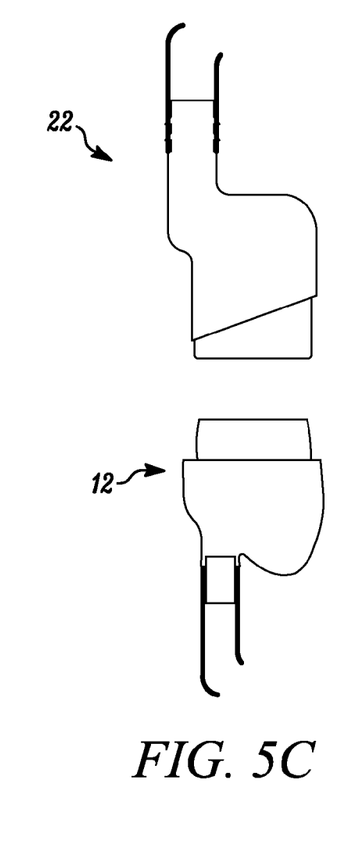
FIG. 5C is a side view of two connectors for varying applications showing differences between the interface, shape and diameter of the male and female connectors to prevent interconnection of such connectors where desired to do so.
Figure 5D:
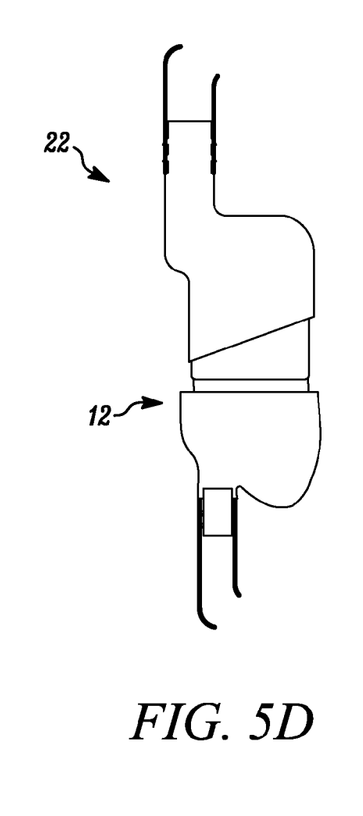
FIG. 5D is a side view of the connectors of FIG. 5C showing the inability of the pairing of the two connectors.

In some embodiments, portions of the connector 10 are formed of different shapes, sizes or ornamental designs to differentiate between various fields of use. In some embodiments, the first connector 12 and second connector 22 have a use-specific diameter. For example, in a hospital setting, connectors 12, 22 for enteral applications may be formed in a first diameter range, while connectors 12, 22 for vascular applications may be formed in a second diameter range, as seen in FIGS. 5A-B. Thus, the different diameters provide a safety mechanism whereby connectors for different applications are incapable of mating with one another. As a result, if a plurality of connectors are present, the suitable pairings are quickly identified and errors in connections are removed.

The connectors also may be formed in different shapes to enable proper connection and bar improper connections. For example, the cross-section of the mating portions of the connectors may be circular for some applications and elliptical, ovoid or any other shape for other applications. Thus, connectors for a first application are only capable of mating with complementary connectors having the same or congruent first cross-section, while connectors for a different application are only capable of mating with complementary connectors having the same or congruent cross-section that is different from the first cross-section. Moreover, the connectors 12, 22 may also include different interfaces for different application as seen in FIG. 5A-D. In some embodiments, the interface of the connectors 12, 22 is selected from a horizontal, curved or angled interface chosen for a specific application. Moreover, a portion of the connectors 12, 22, such as for example, the outer portion, may be formed in a shape indicative of its use as seen in FIGS. 5A-D. For example, a connector for enteral applications may be formed in the shape of a stomach, while a connector for vascular applications may be formed in the shape of a heart. In at least some embodiments, the connectors 12, 22 are formed of complimentary shapes that form a unique shape when combined. For example, as seen in FIG. 5B, the connectors 12 and 22 for vascular applications form the shape of a heart when combined. In addition, the connectors 12, 22 may be manufactured in different colors to indicate different fields of use or applications. Thus, the connectors may be designed to reduce error and improve efficiency in making the correct connections or pairings.

The connectors of the present invention have numerous different applications in any of numerous different fields. For example, the connectors may be used to interconnect intravenous (IV) tubing, pouches and tubing, filling tanks and/or filling machines, and any of numerous other applications requiring fluid connections. As can be readily appreciated, the connectors of the present invention are particularly well suited for applications requiring a clean connection.

As may be recognized by those of ordinary skill in the pertinent art based on the teachings herein, numerous changes, modifications and improvements may be made to the above-described and other embodiments of the present invention without departing from the scope of the invention as defined in the appended claims. For example, the outer portions, central nozzles, obstructive portion and engagement portions, may take any of numerous different configurations that are currently known, or that later become known. In addition, not all elements or all features disclosed herein are necessary, and if desired, additional elements or features may be added. Further, the elements or components of the connectors may be made of any of numerous different materials that are currently known, or that later become known. Still further, the connectors may be used to transport any of numerous different fluids that are currently known, or that later become known, such as drugs, pharmaceuticals, vaccines, ophthalmic products, creams, ointments, gels, beverages or food products, such as dairy, milk, cream, infant formula, chocolate, and industrial products, such as industrial liquids or gases. Accordingly, this detailed description of the currently preferred embodiments is to be taken in an illustrative, as opposed to a limiting sense.

What is claimed is:

1. A connector for transferring a fluid, the connector comprising: a first connector including: a first outer portion including a first obstructive portion and defining a first fluid passageway for receiving a fluid therein; and a first central nozzle coupled to the first outer portion, the central nozzle including a first engagement portion, wherein at least one of the first central nozzle and the first outer portion is rotatably movable relative to the other between a first position and a second position, wherein in the first position the first obstructive portion and the first engagement portion substantially overlap to impede fluid flow through the first fluid passageway, and in the second position, at least one of the first engagement portion and the first obstructive portion is displaced to allow fluid flow through the first fluid passageway; and a second connector including: a second outer portion including a second obstructive portion and defining a second fluid passageway for receiving a fluid therein; and a second central nozzle coupled to the second outer portion, the second central nozzle including a second engagement portion, wherein at least one of the second central nozzle and the second outer portion is rotatably movable relative to the other between a first position and a second position, wherein in the second position the second obstructive portion and the second engagement portion substantially overlap to impede fluid flow through the second fluid passageway, and in the second position, at least one of the second engagement portion and the second obstructive portion is displaced to allow fluid flow through the second fluid passageway; wherein the first and second connectors are engageable and movable between non-connected and connected positions, wherein in the non-connected position, the first fluid passageway and second fluid passageway are obstructed, and in the connected position, the first fluid passageway and second fluid passageway are in fluid communication with one another.

2. A connector as defined in claim 1, wherein the connector is movable to a connected position by coupling the first connector and second connector and rotating at least one of the first connector and second connector relative to the other.

3. A connector as defined in claim 1, wherein one of the engagement portion and the obstructive portion is moved to allow fluid flow through the second fluid passageway.

4. A connector as defined in claim 1, wherein the first central nozzle and the second central nozzle are formed of materials having different shrinkage than the first and second outer portions, respectively, said different shrinkage being selected to define a desired level of friction therebetween.

5. A connector as defined in claim 1, wherein at least a portion of the connector includes an indicator of a field of use.

6. A connectors as defined in claim 5, wherein the indicator is a color.

7. A connectors as defined in claim 5, wherein the indicator is at least one dimension of the first and second connectors.

8. A connectors as defined in claim 5, wherein the indicator is a shape of a portion of the first and second connectors.

9. A connector as defined in claim 1, wherein the first obstructive portion is fixed relative to all other portions of the first outer portion.

10. A connector as defined in claim 1, wherein in the second position the at least one of the first engagement portion and the first obstructive portion is rotationally displaced relative to each other.

11. A connector as defined in claim 1, wherein the second obstructive portion is fixed relative to all other portions of the second outer portion.

12. A connector as defined in claim 1, wherein in the second position the at least one of the second engagement portion and the second obstructive portion is rotationally displaced relative to each other.

13. A method comprising the following steps: (i) positioning or maintaining a first connector connected to one end of a first conduit in a closed position to, in turn, maintain a fluid hermetically sealed within the first conduit, wherein a first nozzle of the first connector is in fluid communication with the first conduit and is recessed within a first housing of the first connector to prevent contamination of the first nozzle, and at least one of the first nozzle and the first housing are rotatably movable relative the other;

(ii) interconnecting the first connector to a second connector connected to one end of a second conduit and positioned in a closed position that maintains the second conduit sealed with respect to ambient atmosphere, wherein a second nozzle of the second connector is in fluid communication with the second conduit and is recessed within a second housing of the second connector to prevent contamination of the second nozzle, and at least one of the second nozzle and the second housing are rotatably movable relative to the other; and (iii) moving at least one of the first and second connectors or portions thereof from the closed to an open position and, in turn, placing the first and second nozzles in fluid communication with each other to allow fluid to flow from the first conduit, through the first and second nozzles, and into the second conduit without exposing the fluid to ambient atmosphere.

14. A method as defined in claim 13, further comprising the step of introducing fluid into the first conduit and, in turn, allowing the fluid to flow from the first conduit, through the first and second nozzles, and into the second conduit without exposing the fluid to ambient atmosphere.

15. A method as defined in claim 13, wherein the interconnecting step includes engaging first and second engagement portions of the first and second nozzles, the moving step includes rotating at least one of the first and second nozzles relative to the other to move from the closed to the open position, and the method further comprising preventing rotation of the first and second engagement portions relative to each other during the interconnecting and moving steps.

16. A method as defined in claim 13, wherein the first and second connectors are formed using a dual sequential injection procedure.

17. A method as defined in claim 13, wherein the moving step includes rotating both the first connector and the second connector.

18. A method as defined in claim 13, wherein the moving step includes at least one of (i) rotating at least one of the first nozzle and the first housing relative to the other, and (ii) rotating at least one of the second nozzle and the second housing relative to the other.

19. A connector system comprising: at least two connectors, each including an outer portion including an obstructive portion and defining a fluid passageway for receiving a fluid therein; and a nozzle coupled to the outer portion, the nozzle including an engagement portion, at least one of the nozzle and the obstructive portion being rotatably movable relative to the other between a first position and a second position, wherein in the first position the obstructive portion and the nozzle substantially overlap to impede fluid flow through the fluid passageway, and in the second position, at least one of the nozzle portion and the obstructive portion is displaced to allow fluid flow through the fluid passageway, wherein the at least two connectors are engageable and movable between non-connected and connected positions, wherein in the non-connected position, the first fluid passageway and second fluid passageway are obstructed, and in the connected position, the first fluid passageway and second fluid passageway are in fluid communication with one another.

* * * * *

UNITED STATES PATENT AND TRADEMARK OFFICE
CERTIFICATE OF CORRECTION

| | | |
|---|---|---|
| PATENT NO. | : 8,746,278 B2 | Page 1 of 1 |
| APPLICATION NO. | : 13/213969 | |
| DATED | : June 10, 2014 | |
| INVENTOR(S) | : Daniel Py | |

It is certified that error appears in the above-identified patent and that said Letters Patent is hereby corrected as shown below:

In the Claims

At column 9, claim 6, line 29, replace the word "connectors" with --connector--.

At column 9, claim 7, line 31, replace the word "connectors" with --connector--.

At column 9, claim 8, line 33, replace the word "connectors" with --connector--.

Signed and Sealed this
Seventh Day of April, 2015

Michelle K. Lee
*Director of the United States Patent and Trademark Office*